United States Patent [19]
Levenson et al.

[11] Patent Number: 6,094,267
[45] Date of Patent: Jul. 25, 2000

[54] OPTICAL HETERODYNE DETECTION FOR CAVITY RING-DOWN SPECTROSCOPY

[75] Inventors: Marc D. Levenson, Saratoga; Barbara A. Paldus, Mountain View; Richard N. Zare, Stanford, all of Calif.

[73] Assignee: The Board of Trustees of the Leland Stanford Jr. University, Palo Alto, Calif.

[21] Appl. No.: 09/295,213

[22] Filed: Apr. 21, 1999

[51] Int. Cl.[7] .................................................. G01B 9/02
[52] U.S. Cl. ................................ 356/349; 356/349
[58] Field of Search ............................... 356/346, 349; 250/343

[56] References Cited

U.S. PATENT DOCUMENTS

| | | |
|---|---|---|
| 4,193,690 | 3/1980 | Levenson et al. . |
| 4,817,101 | 3/1989 | Wyeth et al. . |
| 4,905,244 | 2/1990 | Wyeth et al. . |
| 5,528,040 | 6/1996 | Lehmann . |

OTHER PUBLICATIONS

Levenson, M. et al., Polarization–Selective Optical Heterodyne Detection for Dramatically Improved Sensitivity in Laser Spectroscopy; Applied Phys. 19, pp. 1–17, 1979.

Eesley, G., et al., Optically Heterodyned raman Spectroscopy; IEEE J. of Quantum Electronics, QE–14, pp. 45–48, 1978.

Ultrasensitive High Resolution Laser Spectroscopy and its Application to Optical Frequency Standards; PhD Thesis, Univ. of Colorado at Boulder, Apr. 22, 1997.

Romanini and Lehmann, Cavity ring–down overtone spectroscopy of HCN, H13CN and HC15N, J. Chem. Phys. 102(2):633–642, 1995.

Meijer et al., Coherent cavity ring down spectroscopy, Chem. Phys. Lett. 217(1–2):112–116, 1994.

Zalicki et al., Measurement of the methyl radical concentration profile in a hot–filament reactor, App. Phys. Lett. 67(1):144–146, 1995.

Jongma et al., Trace gas detection with cavity ring doen spectroscopy, Rev. Sci. Instrum. 66(4):2821–2828, 1995.

Zalicki and Zare, Cavity ring–down spectroscopy for quantitative absorption measurements, J. Chem. Phys. 102(7):2708–2717, 1995.

Ye, Jun, et al., Ultrasensitive detections in atomic and molecular physics: demonstration in Molecular overtone spectroscopy, J. Opt. Soc. Am. B, vol. 15, No. 1, 1998, pp. 6–15.

*Primary Examiner*—Samuel A. Turner
*Attorney, Agent, or Firm*—Lumen Intellectual Property Services

[57] ABSTRACT

A cavity ring-down system for performing cavity ring-down spectroscopy (CRDS) using optical heterodyne detection of a ring-down wave $E_{RD}$ during a ring-down phase or a ring-up wave $E_{RU}$ during a ring up phase. The system sends a local oscillator wave $E_{LO}$ and a signal wave $E_{SIGNAL}$ to the cavity, preferably a ring resonator, and derives an interference signal from the combined local oscillator wave $E_{LO}$ and the ring-down wave $E_{RD}$ (or ring-up wave $E_{RU}$). The local oscillator wave $E_{LO}$ has a first polarization and the ring-down wave $E_{RD}$ has a second polarization different from the first polarization. The system has a combining arrangement for combining or overlapping local oscillator wave $E_{LO}$ and the ring-down wave $E_{RD}$ at a photodetector, which receives the interference signal and generates a heterodyne current $I_H$ therefrom. Frequency and phase differences between the waves are adjustable.

36 Claims, 6 Drawing Sheets

OPTICAL HETERODYNE DETECTION FOR CAVITY RING-DOWN SPECTROSCOPY

U.S. GOVERNMENT RIGHTS

This invention was made with U.S. Government support by the Department of Energy and the Air Force under grant numbers DE-FG03-92ER14304 and F49620-97-1-0316, respectively. The U.S. Government has certain rights in this invention.

FIELD OF THE INVENTION

This invention relates to the field of spectroscopy, and in particular to a cavity-ring down system for the determination of ring-down rates by optical heterodyne detection.

BACKGROUND OF THE INVENTION

Traditional spectroscopic methods are limited in sensitivity to approximately one part per ten thousand ($1:10^4$) to one part per hundred thousand ($1:10^5$). The sensitivity limitation arises from instabilities in light source intensity that are translated into noise in the absorption signal. For general information on traditional spectroscopy methods see for example Dereniak and Crowe, *Optical Radiation Detectors*, John Wiley & Sons, New York, 1984, and Demtroder, *Laser Spectroscopy*, Springer, Berlin, 1996.

Cavity Ring-Down Spectroscopy (CRDS), a technique first described by O'Keefe and Deacon in an article in *Rev. Sci. Instrum.* 59(12):2544–2551 (1988), allows one to make absorption measurements with sensitivities on the order of one part per ten million ($1:10^7$) to one part per billion ($1:10^9$) or higher. For general information on CRDS see U.S. Pat. No. 5,528,040 by Lehmann, as well as the articles by Romanini and Lehmann in *J. Chem. Phys.* 102(2):633–642 (1995), Meijer et al. in *Chem. Phys. Lett.* 217(1–2):112–116 (1994), Zalicki et al. in *App. Phys. Lett.* 67(1):144–146 (1995), Jongma et al. in *Rev. Sci. Instrum.* 66(4):2821–2828 (1995), and Zalicki and Zare in *J. Chem. Phys.* 102(7):2708–2717 (1995).

In a CRDS system, the sample (absorbing material) is placed in a high-finesse stable optical resonator or ring-down cavity. Light admitted into the ring-down cavity circulates back and forth multiple times setting up standing waves having periodic spatial variations. Light exiting the ring-down cavity is proportional to the intracavity light intensity.

The radiant energy stored in the ring-down cavity decreases in time (rings-down). For an empty cavity, the stored energy follows an exponential decay characterized by a ring-down rate that depends only on the reflectivity of the mirrors, the separation between the mirrors and the speed light in the cavity. If a sample is placed in the resonator, the ring-down is accelerated; under suitable conditions, the intracavity energy decays almost perfectly exponentially. An absorption spectrum for the sample is obtained by plotting the reciprocal of the ring-down rate $1/\tau$ or of the decay constant $\tau$ versus the wavelength $\lambda$ of the incident light.

In comparison to conventional spectroscopic techniques, CRDS promises to achieve extremely high detection sensitivity because the ring-down rate $1/\tau$ is not a function of the intensity of the incident light. In other words, intensity fluctuations of the incident light are not related to the ring-down rate in the ring-down cavity and thus do not directly affect the CRDS measurement. Theoretically, if CRDS were only limited by shot-noise inherent in any light beam due to the quantum nature of the photons constituting the light beam, the achievable sensitivity would be in the range of $10^{-14}$ $cm^{-1}Hz^{-\frac{1}{2}}$ for a CRDS system having a 50 cm long cavity, a 10 mW continuous-wave (CW) laser with a 10 kHz linewidth and mirrors having losses of 50 ppm.

The actual performance of state-of-the-art CRDS in comparison to other conventional methods is illustrated in Table 1.

TABLE 1

| Spectroscopic Scheme | Typical MDAL ($cm^{-1}$) | Cost | Complexity |
|---|---|---|---|
| Single-pass absorption | $10^{-6}$ | low | simple |
| Multi-pass absorption | $10^{-8}$ | moderate | simple |
| ICLAS | $10^{-6}$–$10^{-11}$ | high | difficult |
| FM | $10^{-6}$–$10^{-8}$ | moderate | moderate to difficult |
| P CRDS | $10^{-6}$–$10^{-10}$ | moderate | simple |
| CW CRDS | $10^{-8}$–$10^{-12}$ | low to moderate | simple to moderate |

ICLAS = intracavity absorption spectroscopy; FM = frequency modulation; P CRDS = pulsed CRDS; CW CRDS = continous-wave CRDS The practical factors limiting sensitivity in P CRDS can be subdivided into three major categories. First, the P CRDS arrangements are limited by optical noise. This noise is due to the limited optical throughput of the ring-down cavity, which is a function of the ratio of the laser and cavity linewidths. In other words, this problem relates to the intensity fluctuations produced during coupling between the laser source and the ring-down cavity. Constant changes in the linewidth ratio affect the signal-to-noise ratio (SNR) at the detector hence producing noise.

Second, CRDS is limited by the quality of the laser beam transverse profile. Ideally, only a single mode-the fundamental $TEM_{00}$ mode-should be excited in the ring-down cavity. Excitation of higher order modes causes a multi-mode excitation condition which imposes a sinusoidal modulation on the ring-down signal beam exiting the ring-down cavity. This causes slow detectors to register a noise band superimposed on the decay signal. In other words, because each mode has slightly different optical losses in the ring-down cavity, the modulation or mode beating will produce a superposition of exponentially decaying signal beams, each having a slightly different decay constant $\tau$.

Hence, trying to determine the decay constant $\tau$ for one particular mode, i.e., the fundamental mode, becomes difficult.

Third, the repetition rate of most pulsed laser systems is limited to 100 Hz, so that extensive averaging to improve sensitivity cannot be performed. Moreover, pulsed lasers tend to be bulky and expensive, and therefore impractical for commercial versions of P CRDS.

In addressing the first problem of P CRDS, CW CRDS uses a narrow line-width CW laser with external modulation to limit the optical noise by achieving high overlap between the laser linewidth and the ring-down cavity linewidth. The second problem of mode beating is limited by optically filtering the CW laser beam profile to almost pure $TEM_{00}$. The third problem of is addressed by using repetition rates in excess of 1 kHz and up to 10 kHz thus permitting averaging operations.

The above improvements introduced in CW CRDS systems to overcome the problems associated with P CRDS have resulted in some improvements in the ability to perform spectral scans in realtime. Still, CW CRDS with direct detection as presently implemented does not allow to reach the true shot-noise limit because of the decaying signal which, no matter how large at the beginning, always decays to zero and hence always hits the detector noise floor. To date, the highest sensitivities obtained for P CRDS and CW CRDS do not approach the theoretical shot-noise limit. The best arrangements for P CRDS reported so far have sensitivities of about $8 \times 10^{-10}$ cm$^{-1}$Hz$^{-\frac{1}{2}}$. The best results obtained for CW CRDS are in the range of $8 \times 10^{-13}$ cm$^{-1}$Hz$^{-\frac{1}{2}}$ using a 10 mW laser. These figures are still far short of the theoretical limits. In fact, in a shot-noise limited CW CRDS system the expected sensitivity is about $1 \times 10^{-14}$ cm$^{-1}$Hz$^{-\frac{1}{2}}$, i.e., almost two orders of magnitude better than state of the art.

In terms of SNR, a ring-down decay signal is ultimately limited by the fluctuations in photon number that occur for a constant power level. For a power level of 1 mW, the shot-noise-limited SNR is $1.8 \times 10^6$:1, while for 1 $\mu$W the SNR is $5.6 \times 10^4$:1. These figures are not achieved by state-of-the-art CRDS.

In striving to achieve higher signal sensitivity and work around noise sources other spectroscopy techniques have resorted to methods such as heterodyning. For example, in U.S. Pat. Nos. 4,817,101 and 4,905,244 Wyeth et al. teach a heterodyne laser spectroscopy system for improved measurement precision. Jun Ye et al. in "Ultrasensitive Detection in Atomic and Molecular Physics: Demonstration in Molecular Overtone Spectroscopy", Journal of the Optical Society of America B, Vol. 15, No. 1, January 1998, pp. 6–15 teach a heterodyne technique building on spectroscopic techniques employing frequency modulation (FM) detection. In U.S. Pat. No. 4,193,690 Marc Levenson et al. teach a heterodyne detection for coherent Raman signals. Additional references include: Marc Levenson et al. "Polarization-Selective Optical Heterodyne Detection for Dramatically Improved Sensitivity in Laser Spectroscopy", *Applied Physics*, 19, pp. 1–17, 1979; Gary Eesley et al. "Optically Heterodyned Raman Spectroscopy", IEEE *Journal of Quantum Electronics*, QE-14, pp. 45–48, 1978; and Jun Ye "Ultrasensitive High-Resolution Laser Spectroscopy and its Application to Optical Frequency Standards", *PhD Thesis*, University of Colorado at Boulder, Apr. 22, 1997.

Unfortunately, the above adaptations of heterodyning are not well-designed to measure exponentially decaying waveforms. In particular, these techniques do not work well for signal detection in CRDS.

OBJECTS AND ADVANTAGES OF THE INVENTION

In light of the above, it is a primary object of the present invention to provide a cavity ring-down system designed for optical heterodyne detection of the ring-down wave. In particular, it is an object of the invention to improve the detection sensitivity of a cavity ring-down system to approach the shot-noise limit through optical heterodyne detection.

It is another object of the invention to adapt the heterodyne detection to continuous-wave CRDS in an easy-to-implement manner.

Yet another object of the invention is to ensure that the optical heterodyne detection system is compatible with other noise reducing measures used in CRDS.

The above objects and advantages, as well as numerous additional improvements attained by the heterodyne detection system of the invention are pointed out below.

SUMMARY OF THE INVENTION

The objects and advantages of the invention are attained by a cavity ring-down system for performing cavity-ring down spectroscopy (CRDS) through optical heterodyne detection of a ring-down wave $E_{RD}$. The decay or ring-down of ring-down wave $E_{RD}$ takes place at a first decay rate $1/\tau$, where $\tau$ is the decay constant. The ring-down system has a light source, preferably a laser, for providing a light beam. A set of optics receives the light beam and generates from it a local oscillator wave $E_{LO}$ at a local oscillator frequency $\nu_{LO}$. The set of optics also generates from the light beam a signal wave $E_{SIGNAL}$ having a signal frequency $\nu_{SIGNAL}$.

The ring-down system has a ring-down cavity positioned in the path of the local oscillator wave $E_{LO}$ and the signal wave $E_{SIGNAL}$. The two waves are admitted into the ring-down cavity through an appropriate input coupler, i.e., a mirror. The ring-down cavity contains the sample whose absorption is being studied.

To perform the ring-down measurement a switching means, e.g., an acousto-optic modulator, and electro-optic modulator or other deflecting device, is used to interrupt the signal wave $E_{SIGNAL}$. Once signal wave $E_{SIGNAL}$ is interrupted the ring-down cavity enters a ring-down phase during which the exponentially decaying ring-down wave $E_{RD}$ issues from it.

While emitting the ring-down wave $E_{RD}$ the ring-down cavity also transmits or reflects the local oscillator wave $E_{LO}$. These two waves exiting the ring-down cavity are intercepted by an optical combining arrangement and made to overlap to thus produce an interference signal. The interference signal contains among its frequency components a heterodyne frequency related to a frequency difference $\delta\nu$ between the local oscillator frequency and the signal frequency ($\delta\nu = |\nu_{LO} - \nu_{SIGNAL}|$). The frequency difference $\delta\nu$ can have any suitable value, depending on the arrangement. In one embodiment frequency difference $\delta\nu$ is set equal to the free spectral range of the ring-down cavity.

In the preferred embodiment the set of optics has polarizing elements for imparting the local oscillator wave $E_{LO}$ with a first polarization and the ring-down wave $E_{RD}$ with a second polarization different from the first polarization, e.g., orthogonal to the first polarization. The combining arrangement in this case includes a polarization rotator such as a birefringent wave plate for rotating these polarizations and a beam splitter for overlapping the two rotated polarizations. Alternatively, a polarizing beam splitter oriented at an appropriate angle can be used by itself to overlap the two waves.

The preferred embodiment uses a continuous wave (CW) laser as the light source and a locking mechanism for locking the ring-down cavity to the laser. The local oscillator wave $E_{LO}$ with the first polarization is used by the locking mechanism to achieve the laser to cavity locking. It is also preferred that the system use a ring resonator as the ring-down cavity.

The photodetector for receiving the interference signal is advantageously placed at a point of maximum overlap between the local oscillator wave $E_{LO}$ and the ring-down wave $E_{RD}$. The photodetector generates a heterodyne current $I_H$ corresponding to the heterodyne component of the interference signal. The heterodyne current $I_H$ has a second decay rate $1/2\tau$. It is desirable to set the intensity of the local oscillator wave $E_{LO}$ higher, and preferably much higher, than an initial intensity, i.e., the peak intensity at the onset of the exponential decay of the ring-down wave $E_{RD}$ Doing this maximizes the heterodyne current $I_H$.

The system of the invention is also equipped with a phase adjustment mechanism for adjusting the relative phase between the local oscillator wave $E_{LO}$ and the ring-down wave $E_{RD}$. Furthermore, the system has a frequency adjustment means for adjusting the frequency difference $\delta v$ between these waves.

In an alternative embodiment the system employs a modulator for altering the signal frequency $v_{SIGNAL}$ of signal wave $E_{SIGNAL}$.

Changing the signal frequency $v_{SIGNAL}$ initiates the ring-down phase in this embodiment. In yet another alternative embodiment, the locked system is used to measure the interference signal during cavity ring-up rather than ring-down phase.

Further details of the optical heterodyne system are found below in the description with reference to the attached drawing figures.

DETAILED DESCRIPTION

Figure 1:
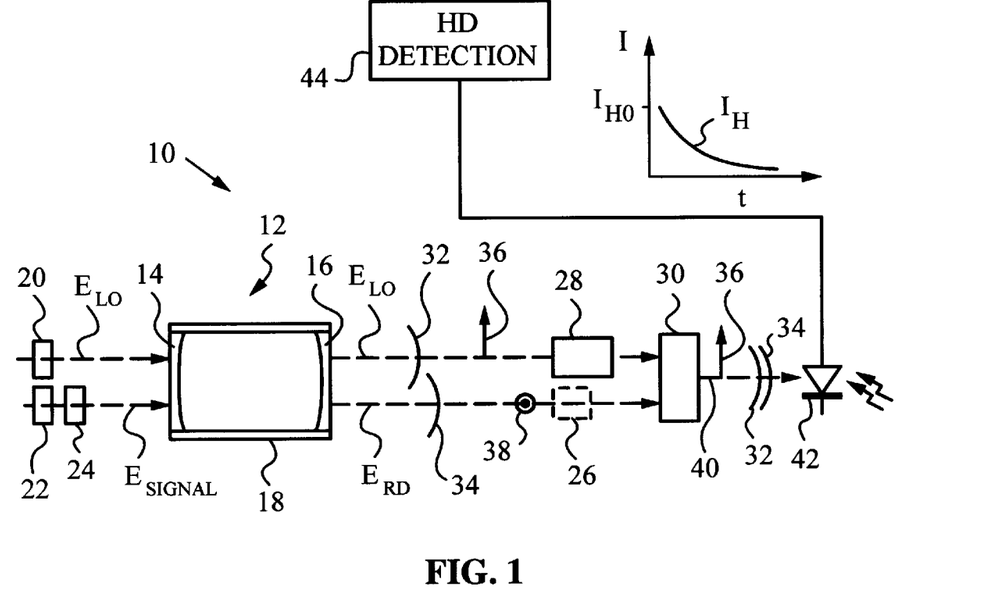
FIG. 1 is a general schematic diagram of a cavity ring-down system for optical heterodyne detection.
Figure 2:
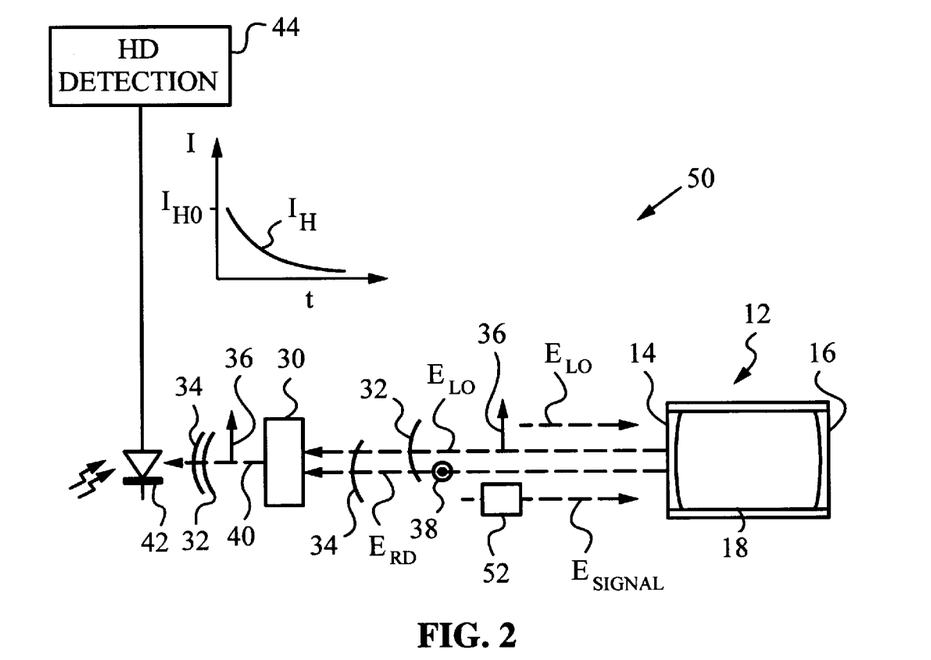
FIG. 2 is a general schematic diagram of another cavity ring-down system for optical heterodyne detection.

FIG. 1 and FIG. 2 present general schematic diagrams of two types of cavity ring-down systems according to the invention. Review of these general types of systems elucidates the basics of optical heterodyne detection in cavity ring-down spectroscopy (CRDS) and is useful in understanding the preferred embodiment and the alternative embodiments presented below.

FIG. 1 shows a cavity ring-down system 10 equipped with a ring-down cavity 12 having an input coupler 14 and an output coupler 16. In this case cavity 12 is a linear cavity enclosed in a gas-tight housing 18 for measuring the absorption of a gas sample (not shown). To ensure high sensitivity measurement, cavity 12 is a high finesse cavity. For example, cavity 12 has a finesse value of 1,000 to 1,000,000.

A set of optics consisting of elements 20 and 22 generate a local oscillator wave $E_{LO}$ and a signal wave $E_{SIGNAL}$ respectively. Local oscillator wave $E_{LO}$ has a local oscillator frequency $v_{LO}$ and signal wave $E_{SIGNAL}$ has a signal frequency $v_{SIGNAL}$. There is a frequency difference $\delta v$ between the local oscillator and signal frequencies.

Waves $E_{LO}$ and $E_{SIGNAL}$ are coupled into ring-down cavity 12 through input coupler 14. Frequencies $v_{SIGNAL}$ and $v_{LO}$ are selected such that both are resonant in ring-down cavity 12 simultaneously. System 10 has a switching element 24, e.g., an acousto-optic or electro-optic modulator, positioned in the path of signal wave $E_{SIGNAL}$. Switching element 24 is used for interrupting signal wave $E_{SIGNAL}$ when sufficient light buildup for performing a ring-down measurement is achieved within cavity 12.

During the ring-down measurement cavity 12 is in a ring-down phase and a ring down wave $E_{RD}$ issues through output coupler 16. Local oscillator wave $E_{LO}$ is not interrupted during the ring-down phase and issues through output coupler 16 throughout the ring-down phase.

A phase modulator 26 (indicated in a dashed line) may be positioned behind output coupler 16 in the path of ring-down wave $E_{RD}$. A frequency adjustment unit or modulator 28 is positioned behind output coupler 16 in the path of local oscillator wave $E_{LO}$. These are standard devices well-known in the art. Their purpose is to adjust the relative phase and frequency difference $\delta v$ between local oscillator wave $E_{LO}$ and ring-down wave $E_{RD}$. A person of average skill in the art will appreciate that the positions of modulators 26 and 28 can be interchanged. In fact, a separate phase and frequency modulator can be used for each wave, as necessary, to achieve adjustment of relative phase and frequency difference $\delta v$. It is also possible to keep frequency difference $\delta v$ at zero or nearly zero and control the phases of the ring-down wave $E_{RD}$ and the local oscillator wave $E_{LO}$.

A beam combining optic 30 is located behind modulators 26, 28 for receiving local oscillator wave $E_{LO}$ and ring-down wave $E_{RD}$ and overlapping them. In particular, waves $E_{LO}$ and $E_{RD}$ may have wave fronts 32 and 34 and orthogonal polarizations 36 and 38. Optic 30 is designed to overlap wave fronts 32 and 34 and rotate one or both polarizations 36 and 38 to achieve overlap between these polarizations of waves $E_{LO}$ and $E_{RD}$ and thus produce an interference signal 40. It is very important for heterodyne detection according to the invention that good overlap between waves $E_{LO}$ and $E_{RD}$ is achieved. In this case optic 30 projects polarization 38 and polarization 36 to the intermediate state of interference wave or signal 40.

A photodetector 42, e.g., a phototransistor, photodiode or an equivalent device is positioned in the path of interference signal 40. The exact position of photodetector 42 should be at the point of maximum overlap between waves $E_{LO}$ and $E_{RD}$. The function of photodetector 42 is to produce an electrical signal, e.g., a current, proportional to interference signal 40. Amplifiers and additional electronics required to amplify and process the current from photodetector 42 are known to a person of average skill in the art and are not shown. A heterodyne detection circuit 44 is connected to photodetector 42 to receive the electrical signal corresponding to interference signal 40.

During operation, system 10 is first activated for a sufficient amount of time to achieve light buildup inside cavity 12. In other words, waves $E_{LO}$ and $E_{SIGNAL}$ are coupled into cavity 12 until signal wave $E_{SIGNAL}$ is built up to a sufficient intensity within cavity 12. Then, switch 24 shuts off or interrupts signal wave $E_{SIGNAL}$ to initiate the ring-down phase.

During the ring-down phase heterodyne detection of system 10 is active. A person of average skill in the art will appreciate that heterodyne detection may be shut off or gated during the light buildup stage or be active, as convenient. Suitable electronics for performing the gating function are known in the art.

During detection good spatial and polarization overlap of ring-down wave $E_{RD}$ with local oscillator wave $E_{LO}$ at the location where interference signal 40 impinges on photodetector 42 is important. Given frequency difference $\delta v$ between local oscillator wave $E_{LO}$ and ring-down wave $E_{RD}$ the current produced by interference signal 40 in photodetector 42 is proportional to the absolute square of the total field amplitude of waves $E_{LO}$ and $E_{RD}$, which can be separated into three terms as follows:

$$I_D \propto |\overline{E}_{RD} + e^{-i(2\pi\delta vt+\Phi)}\overline{E}_{LO}|^2 =$$
$$|\overline{E}_{RD}|^2 + |\overline{E}_{LO}|^2 + 2\text{Re}[e^{-i(2\pi\delta vt+\Phi)}\overline{E}_{LO}^* \cdot \overline{E}_{RD}].$$

The third electric field term in the rightmost expression represents an optical heterodyne field contained in interference signal 40. The heterodyne frequency of the optical heterodyne field contained in interference signal 40 depends on the frequency difference $\delta v$. $\Phi$ is a phase difference which depends on the optical path length difference between local oscillator wave $E_{LO}$ and ring-down wave $E_{RD}$.

The three electric fields from the above equation produce corresponding current components in photodetector 42 as follows:

$$I_D \propto I_{RD} + I_{LO} + |I_{H0}|\cos(2\pi\delta vt + \Phi).$$

Current components $I_{RD}$ and $I_{LO}$ are the ring-down current and the local oscillator current. They are produced by waves $E_{RD}$ and $E_{LO}$ respectively. The third current component is a heterodyne current $I_H$ corresponding to the optical heterodyne field.

In prior art, direct current detection CRDS or homodyne detection CRDS no heterodyne current $I_H$ is present and the decay rate $1/\tau$ is determined from the current proportional to $E_{RD}$, i.e., $I_{RD}$. In other words, direct detection method measures ring-down current $I_{RD}$ which decays exponentially in time and is generally expressed as:

$$I_{RD}(t) = e^{-t/\tau}.$$

$I_{RD}$ is typically a very low current requiring significant amplification and thus exposing the prior art systems to significant electronic noise. Even if optical noise sources, such as those discussed in the background section, are effectively suppressed, the electronic noise associated with detection and amplification of ring-down current $I_{RD}$ presents a barrier to sensitive measurements of the decay rate $1/\tau$.

The present invention improves measurement sensitivity by measuring $I_H$ rather than $I_{RD}$. Specifically, in accordance with the invention, the intensity of local oscillator wave $E_{LO}$ is set significantly larger than the initial intensity of exponentially decaying ring-down wave $E_{RD}$. This ensures that the initial amplitude $I_{H0}$ of heterodyne current $I_H$ produced by photodetector 42 is maximized to improve detection sensitivity. Preferably, the intensity of wave $E_{LO}$ is adjusted such that the initial amplitude of heterodyne current $I_H$ is:

$$|I_{H0}| = 2\sqrt{I_{LO}I_{RD}}.$$

Under these conditions heterodyne current $I_H$ as a function of time can be expressed as:

$$I_H(t) = 2\sqrt{I_{LO}I_{RD}}\cos(2\pi\delta vt + \Phi)$$

at t<0 or before the onset of the ring-down phase, and $$I_H(t) = 2\sqrt{I_{LO}I_{RD}}\cos(2\pi\delta vt + \Phi)e^{-t/2\tau}$$

at t>0 or during the ring-down phase. Preferably, phase modulator 26 is used to compensate for phase difference $\Phi$. For example, phase difference $\Phi$ is set equal to zero or to an integer multiple of $\pi$. Under these conditions phase difference $\Phi$ can be left out of the equation.

Interference signal 40 thus produces heterodyne current $I_H$ having a heterodyne frequency dependent on frequency difference $\delta v$. The exponential decay of heterodyne current $I_H$ is governed by a second decay rate $1/2\tau$ rather than the decay rate $1/\tau$ of ring-down wave $E_{RD}$. Consequently, heterodyne current $I_H$ decays twice slower than ring-down current $I_{RD}$, thus permitting a more sensitive measurement of the decay rate $1/\tau$ by heterodyne circuit 44. Specifically, circuit 44 first measures the slower decaying second decay rate $1/2\tau$ and then determines from it by direct calculation first decay rate $1/\tau$ or the decay rate of ring-down wave $E_{RD}$. The electronics for performing these calculations can include analog or digital circuitry. In fact, analog circuitry is preferred for calculating exponentially decaying signals. For more details refer to T. G. Spence et al., "Approaching the Shot-Noise Limit for Large Signals in Cavity Ring-Down Spectroscopy Using Analog Detection Electronics", Journal of the *Optical Society of America*, February 1999.

The absorption of gas sample located inside cavity 12 is determined from the decay rate $1/\tau$, as known in the art. Hence, a more accurate determination of the decay rate $1/\tau$ permits one to make a more accurate determination of the absorption of the gas sample.

Since cavity 12 is a high-finesse cavity both waves $E_{LO}$ and $E_{RD}$ exiting from cavity 12 are high quality. This means that these two waves are accurately directed along their optical paths to combiner 30 and their frequencies, $v_{LO}$ and $v_{SIGNAL}$, are very precise due to the well-known filtering effect of high-finesse cavity 12. Under these conditions the signal to noise ratio (SNR) of heterodyne current $I_H$ will approach the shot-noise limit of the quantum noise present in $E_{RD}$ wave when the electronic parameters of photodetector 42 and circuit 44 are optimized according to well-known electronics principles. In particular, the noise power of photodetector 42 and of circuit 44 have to be low, and the shot-noise of local oscillator current $I_{LO}$ have to be minimized.

FIG. 2 illustrates another general schematic of a cavity ring-down system 50. The same elements are designated by the save reference numerals as in FIG. 1. System 50 differs from system 10 in that it overlaps waves $E_{LO}$ and $E_{RD}$ reflected from ring-down cavity 12 rather than transmitted through cavity 12. To initiate the ring-down phase system 50 uses a frequency modulator 52 which shifts signal frequency $v_{SIGNAL}$ of wave $E_{SIGNAL}$ such that it is no longer admitted into cavity 12. Otherwise, system 50 operates in the same manner as system 10, by obtaining heterodyne current $I_H$ from overlapped waves $E_{RD}$ and $E_{LO}$.

Figure 3:
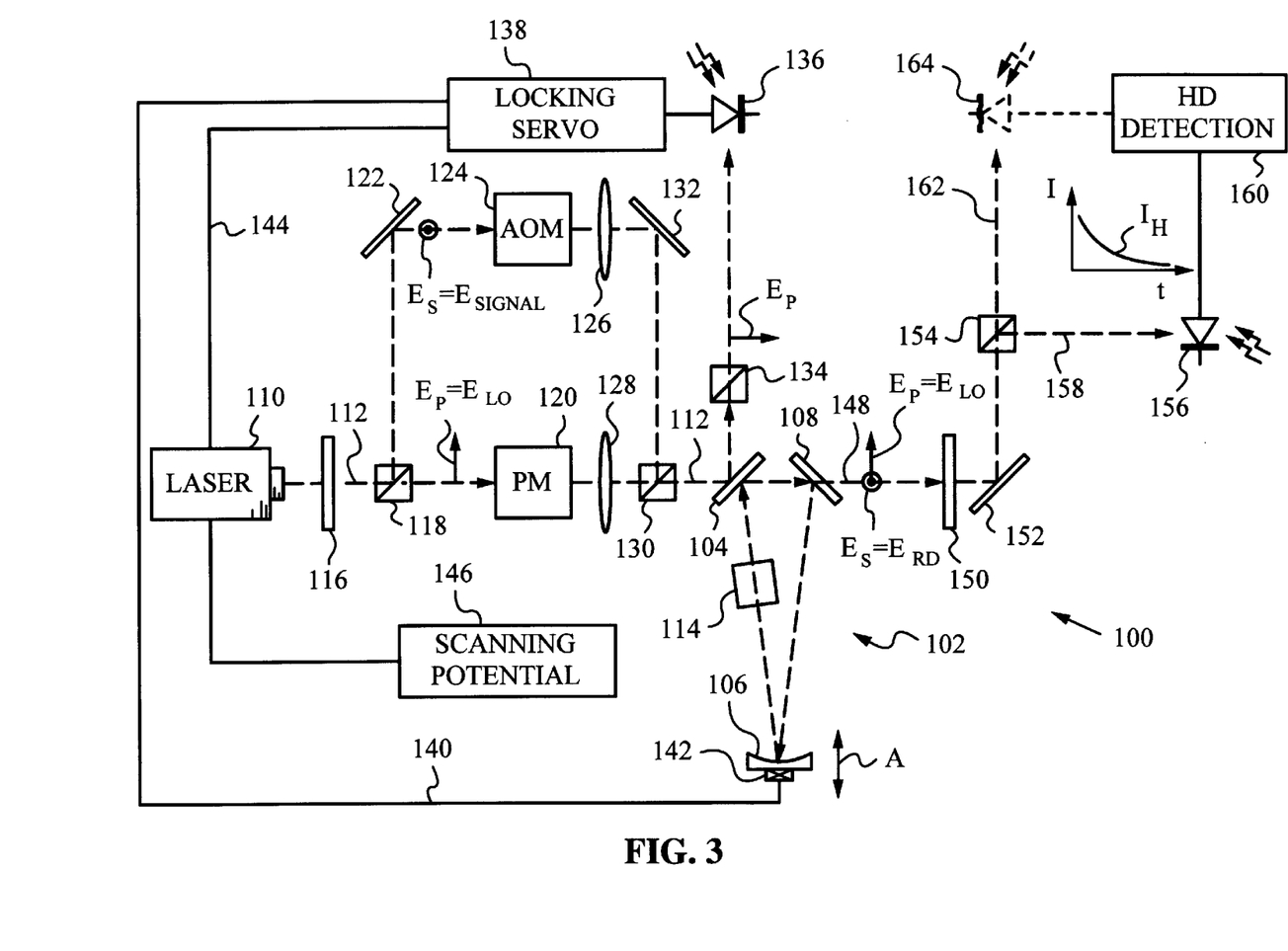
FIG. 3 is a schematic diagram of a preferred embodiment of a system according to the invention.

FIG. 3 illustrates a preferred implementation of a cavity ring-down system 100 for optical heterodyne detection according to the general principles explained above. System 100 has a high finesse ring-down cavity 102 set up between three mirrors 104, 106 and 108. Cavity 102 may be located within an enclosure if designed for measuring the absorption of gases or it may not have an enclosure if designed for measuring non-volatile samples, e.g., thin films.

Mirror 104 is a plano-plano mirror serving as an input coupler and mirror 108 is a plano-plano mirror serving as an output coupler. Mirror 106 is a concave mirror. Ring-down cavity 110 has a ring resonator geometry, which is the most preferred type of cavity for practicing CRDS.

A pump laser 110 which is preferably a high-quality, narrow linewidth laser tunable over a wavelength range of interest provides a light beam 112. In particular, pump laser 110 generates a pump beam 112 whose wavelength range is selected to include the absorption peak(s) of interest of an absorptive sample 114 placed in ring-down cavity 102. For example, laser 110 is a Nd:YAG laser having an output power of 300 mW and a tunable range from 1064.44 nm to 1064.58 nm. This wavelength range permits one to study an absorption spectrum of a $CO_2$ transition at 1064 nm. Of course, this is an exemplary range used for demonstration purposes.

A half-wave plate 116 followed by a polarizing beam splitter (PBS) 118 are placed in the path of beam 112. Beam 112 contains an s-polarization $E_S$ and a p-polarization $E_P$ with respect to ring-down cavity 102. Polarizations $E_S$ and $E_P$ are orthogonal to each other and their relative intensities can be adjusted with the aid of half-wave plate 116. Polarization $E_S$ of beam 112 is used as a signal wave $E_{SIGNAL}$, and polarization $E_P$ serves the function of a local oscillator wave $E_{LO}$.

PBS 118 separates polarization $E_S$ from polarization $E_P$. Polarization $E_P$ is passed to a phase modulator (PM) 120 while polarization $E_S$, after reflection from a mirror 122, is passed to an acousto-optic modulator (AOM) 124. In this preferred arrangement embodiment AOM 124 has two functions. First, it frequency shifts polarization $E_S$ as necessary to allow both polarizations $E_P$ and $E_S$ to be simultaneously resonant in ring-down cavity 102. In other words, AOM controls a frequency difference $\delta v$ between polarizations $E_P$ and $E_S$; difference $\delta v$ should be equal to the free spectral range of cavity 102. Second, AOM 124 is also used to switch polarization $E_S$ on and off, i.e., AOM 124 is used to terminate polarization $E_S$ at required times to initiate the ring-down phase of cavity 102.

PM 120 is used to generate feedback from ring-down cavity 102 to allow one to lock laser 110 to cavity 102. This can be performed in accordance to the Drever technique described by R. Drever et al. in *Applied Physics B*, 1983, B31, pg. 1997.

Both polarizations $E_S$ and $E_P$ pass through mode-matching optics 126, 128 generally indicated by lenses, and are recombined as beam 112 by a PBS 130 after polarization $E_S$ is reflected by a mirror 132. Mode-matching optics 126, 128 ensure modal purity of recombined beam 112. Ideally, recombined beam 122 is in the $TEM_{00}$ mode thus eliminating mode-beating and the associated optical noise sources.

Beam 112 is injected into ring-down cavity 102 through input coupler 104. $E_S$ polarization is used for absorption measurement and $E_P$ polarization is used for locking laser 110 to cavity 102 and as local oscillator wave $E_{LO}$. Since cavity 102 is a ring resonator $E_P$ and $E_S$ polarizations reflected by cavity 102 do not retrace the path of original beam 112. Hence, well-known feedback problems associated with portions of pump beam 112 being reflected back to laser 110 are avoided. Instead, $E_P$ and $E_S$ polarizations reflected from cavity 102 pass through input coupler 104 at an angle to beam 112 and $E_P$ polarization is isolated from $E_S$ polarization by a PBS 134.

Reflected $E_P$ polarization is detected by a photodetector or photodiode 136 and converted into an adjustment signal. The adjustment signal from photodiode 136 may be amplified by an amplifier (not shown) as necessary and delivered to a locking servo 138. Locking servo 138 uses the adjustment signal to lock laser 110 to cavity 102.

In fact, servo 138 sends a high frequency portion of the adjustment signal via connection 140 to a first actuator 142, e.g. a piezoelectric actuator (PZT). PZT 142 moves mirror 106 as indicated by arrow A and thereby adjusts the length of cavity 102. This adjustment is performed for high frequency disturbances, e.g., in the kHz range. In the present embodiment the unity gain frequency, i.e., the center frequency for high frequency adjustments was set at 60 kHz. Low frequency adjustment signals are divided into very low and low frequency; the first having unity gain at 1 Hz and the second having unity gain at 100 Hz. The very low frequency adjustment signals are delivered via connection 144 to the temperature control (not shown) of laser 110. The temperature control adjusts the temperature of laser 110 and thus adjusts the wavelength of beam 112. The low frequency adjustment signals are sent to PZT 142 via connection 140 to adjust the length of cavity 102.

A person of average skill in the art will recognize that this method of locking laser 110 to cavity 102 may be modified in many ways. Also, other locking techniques known in the art may be utilized. However, it is important that laser 110 be locked to cavity 102 with sufficient accuracy ensure a high and stable optical throughput of light through cavity 102. In other words, the locking should overcome the problem of intensity fluctuations produced during coupling between laser 110 and cavity 102, thus eliminating coupling-related noise described in the background section. Furthermore, the locking should be stable for a sufficiently long period of time, i.e., for a period of at least one scan of sample 114.

A scanning unit 146 is connected to laser 110 for the purpose of tuning the wavelength of beam 112 over the tunable range. Of course, varying the length of cavity 102 with the aid of PZT 142 can also be employed for altering the resonant wavelength within cavity 102 and thus achieving some wavelength tuning or scanning. Typically, however, high speed scans (e.g., in the ranges of hundreds of MHz/s) are most effectively performed with the aid of unit 146. A person of average skill in the art will recognize and implement the most viable scanning method in a given situation.

Once sufficient light buildup in cavity 102 is achieved, AOM 124 is switched to interrupt the passage of $E_S$ polarization. When this is done, $E_S$ polarization built-up inside cavity 102 rings down. In particular, a ring-down beam 148 containing both $E_S$ and $E_P$ polarizations corresponding to a ring-down wave $E_{RD}$ and local oscillator wave $E_{LO}$ issues from cavity 110 during the ring-down phase.

A birefringent plate 150 and a PBS 154 positioned in the path of ring-down beam 148 serve as an optical combiner. The function of the optical combiner is to rotate polarizations $E_S$ and $E_P$, or waves $E_{RD}$ and $E_{LO}$ in order to produce a projection whose amplitude is proportional to the product of $E_S$ and $E_P$, or $E_{RD}$ and $E_{LO}$. For example, plate 150 rotates polarizations $E_S$ and $E_P$, or waves $E_{RD}$ and $E_{LO}$, by 45°. A mirror 152 reflects the rotated waves $E_{RD}$ and $E_{LO}$ to PBS 154 which reflects 50% of each wave to a photodetector 156. In this manner waves $E_{RD}$ and $E_{LO}$ are overlapped in an interference signal 158.

To ensure maximum overlap of waves $E_{RD}$ and $E_{LO}$ at the position of photodetector 156 the position of the latter may be adjusted.

Also, PM 120 as well as AOM 124 may be tuned to achieve precise overlap of the wave fronts of $E_{RD}$ and $E_{LO}$ waves. Preferably, PM 120 serves to eliminate phase difference $\Phi$ between waves $E_{RD}$ and $E_{LO}$. AOM 124 is used to fine tune frequency difference $\delta v$. The optimal settings of all elements can be determined by monitoring a heterodyne current $I_H$ generated by photodetector 156.

A heterodyne detection circuit 160 receives heterodyne current $I_H$ and determines from it the second decay rate $1/2\tau$, as described above. Preferably, a transimpedance amplifier (not shown) is used to amplify $I_H$ generated by photodetector 156 before delivering it to detection circuit 160.

Photodetector 156 captures interference signal 158 which contains only half of all light resulting from overlapping $E_{RD}$ and $E_{LO}$. The other half is transmitted through PBS 154 in the form of a second interference signal 162. As indicated in dashed lines, a second photodetector 164 can be provided to capture second interference signal 162 and generate a second heterodyne current $I_H$. The two heterodyne currents can be added together in heterodyne detection circuit 160 to obtain a twice larger current signal. This type of dual-detector heterodyne detection technique (using photodetectors 156 and 164) produces a stronger heterodyne current $I_H$, but is prone to additional noise. A person skilled in the art will recognize that careful balancing should be ensured when operating system 100 in the dual-detector mode.

Figure 6:
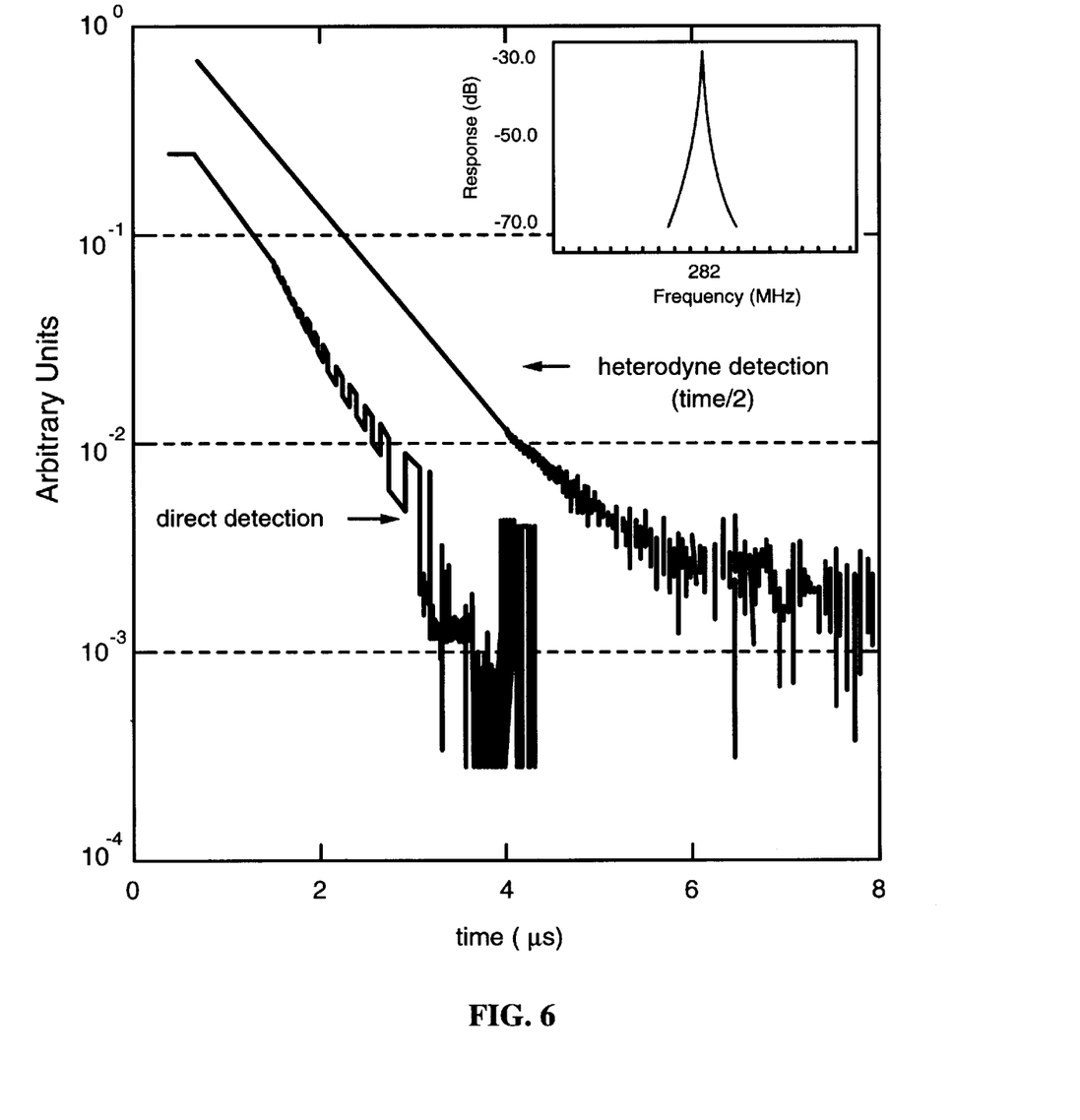
FIG. 6 is a graph comparing the performance of optical heterodyne detection according to the invention with prior art homodyne detection.
Figure 7:
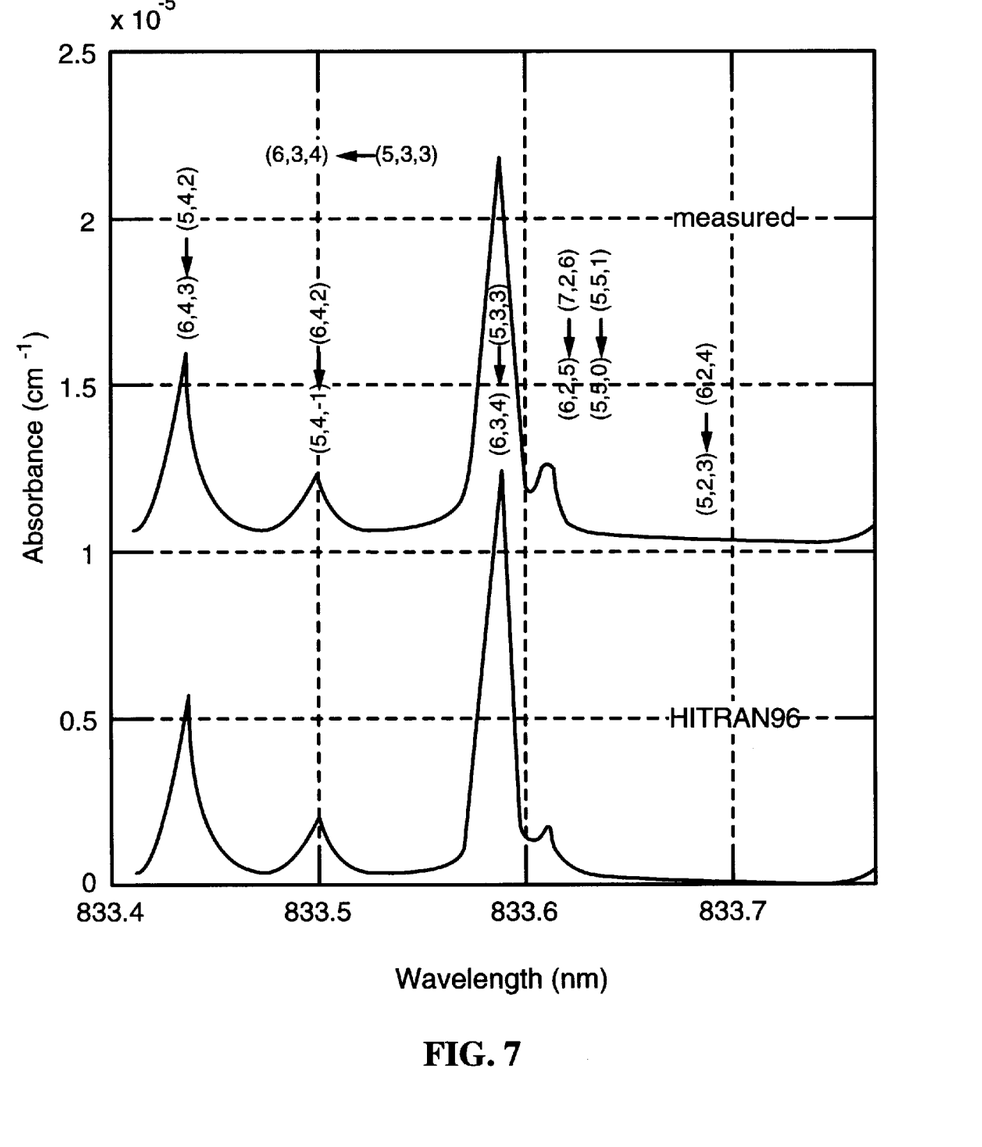
FIG. 7 is a graph illustrating an absorption spectrum obtained with the system of the invention.

The performance of system 100 using single photodetector 156 is illustrated by the graphs in FIGS. 6 and 7. FIG. 6 compares the graphs for 256 ring-down decays for direct or homodyne detection and heterodyne detection. The time scale for the heterodyne detection graph is halved to equalize decay times. The inset shows signal power levels for heterodyne detection. System 100 achieves an SNR increase of up to 31 dB over direct detection. A person of average skill in the art will recognize that further improvements in the electronics will allow system 100 to reach true shot-noise-limited sensitivity. Under this condition the sensitivity and precision with which the absorption coefficients of sample 114 can be measured will depend only on the length of cavity 102, reflectivity of mirrors 104, 106 and 108 and laser noise statistics of laser 110. With current technology (mirror reflectivity of 99.999% and maximum cavity throughput in the range of hundreds $\mu$W) the absorption sensitivity using heterodyne detection according to the invention can yield absorption sensitivity and precision of about $\Delta\alpha=10^{-13}$ cm$^{-1}$ for a single decay measurement. With such absorption sensitivity it is possible to detect only a few thousand molecules inside the volume of beam 112 on typical IR absorption features.

FIG. 7 shows the spectrum of water vapor obtained in room air in comparison to accepted data published in HITRAN96. The sensitivity of system 100 to water vapor at atmospheric pressure is about 1 part per million. The root-mean-square (RMS) baseline noise is $\Delta\alpha=10^{-9}$ cm$^{-1}$ based on 256 decay measurements.

In addition to increased measurement sensitivity, system 100 is easy to implement and permits the use of other noise reducing measures. In particular, system 100 takes advantage of laser to cavity locking and mode shaping. This makes system 100 attractive for practical CRDS implementations.

Figure 4:
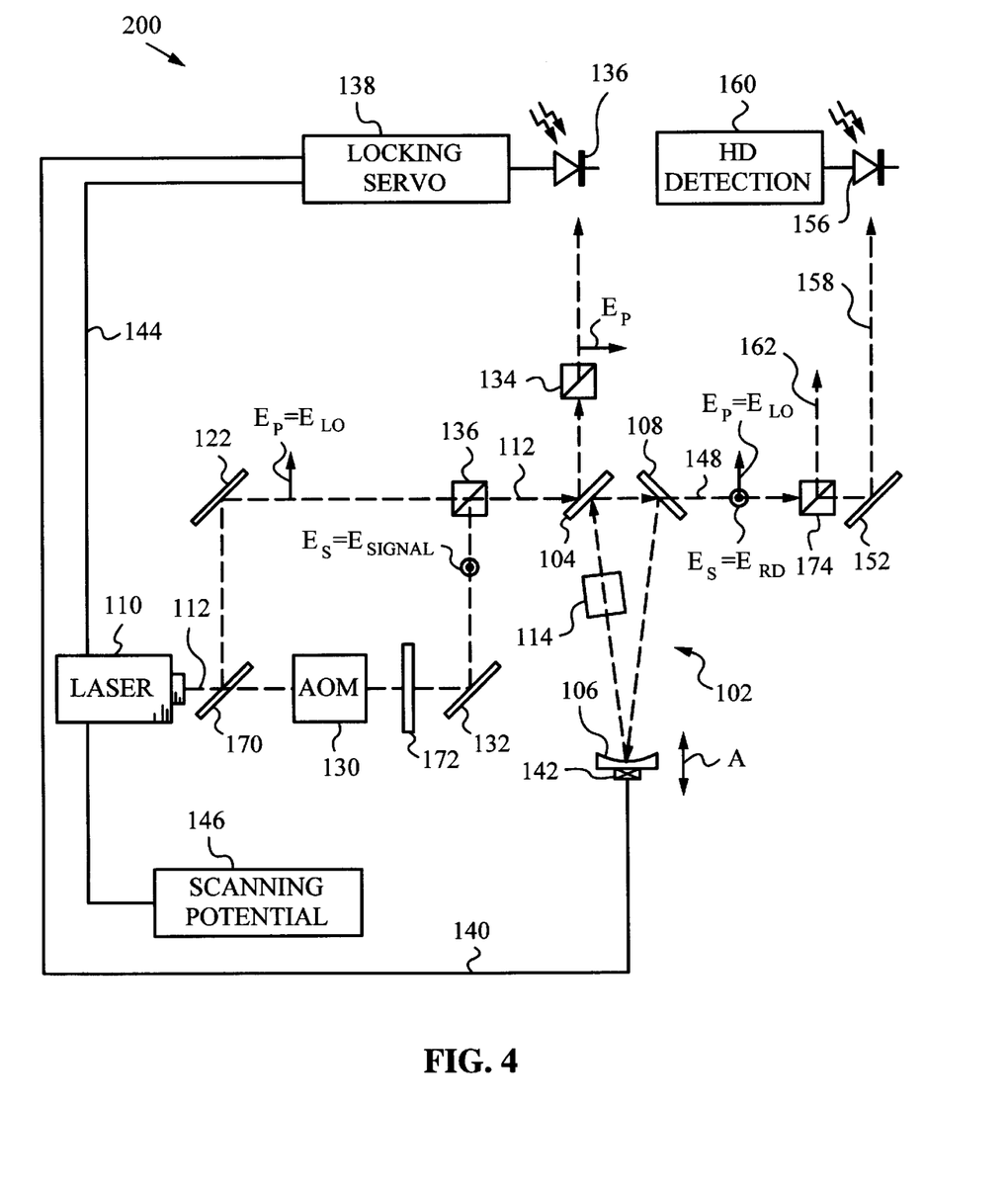
FIG. 4 is a schematic diagram of an alternative embodiment of a system according to the invention.

FIG. 4 shows an alternative cavity ring-down system 200. Corresponding parts are referenced with the same reference numbers as in FIG. 3. As in the preferred embodiment, system 200 is supplied by light beam 112 from laser 110. Beam 112 is split into $E_S$ and $E_P$ polarizations serving as signal wave $E_{SIGNAL}$ and local oscillator wave $E_{LO}$ by a splitter 170. AOM 130 and a birefringent plate 172 are used to adjust signal frequency $\nu_{SIGNAL}$ and $E_S$ polarization.

$E_P$ and $E_S$ polarizations are recombined in beam 112 by PBS 136. Beam 112 is injected into cavity 102. Reflected $E_P$ polarization is used for locking laser 110 to cavity 102, as in the preferred embodiment, with the aid of PBS 134, photodetector 136 and locking servo 138.

AOM 130 is used to interrupt $E_S$ polarization or signal wave $E_{SIGNAL}$ to start the ring-down phase of cavity 102. Ring-down beam 148 issuing from cavity 102 during the ring-down phase contains orthogonal polarizations $E_P$ and $E_S$. System 200 employs a single PBS 174 oriented at about 45° as a combiner for overlapping polarizations $E_P$ and $E_S$ to create interference signal 158. As in the preferred embodiment, 50% of the total light of ring-down beam 148 is contained in interference signal 158 sent to photodetector 156. The remaining light is reflected by PBS 174 in second interference signal 162 which may or may not be used for heterodyne detection (not used in the embodiment shown).

Figure 5:
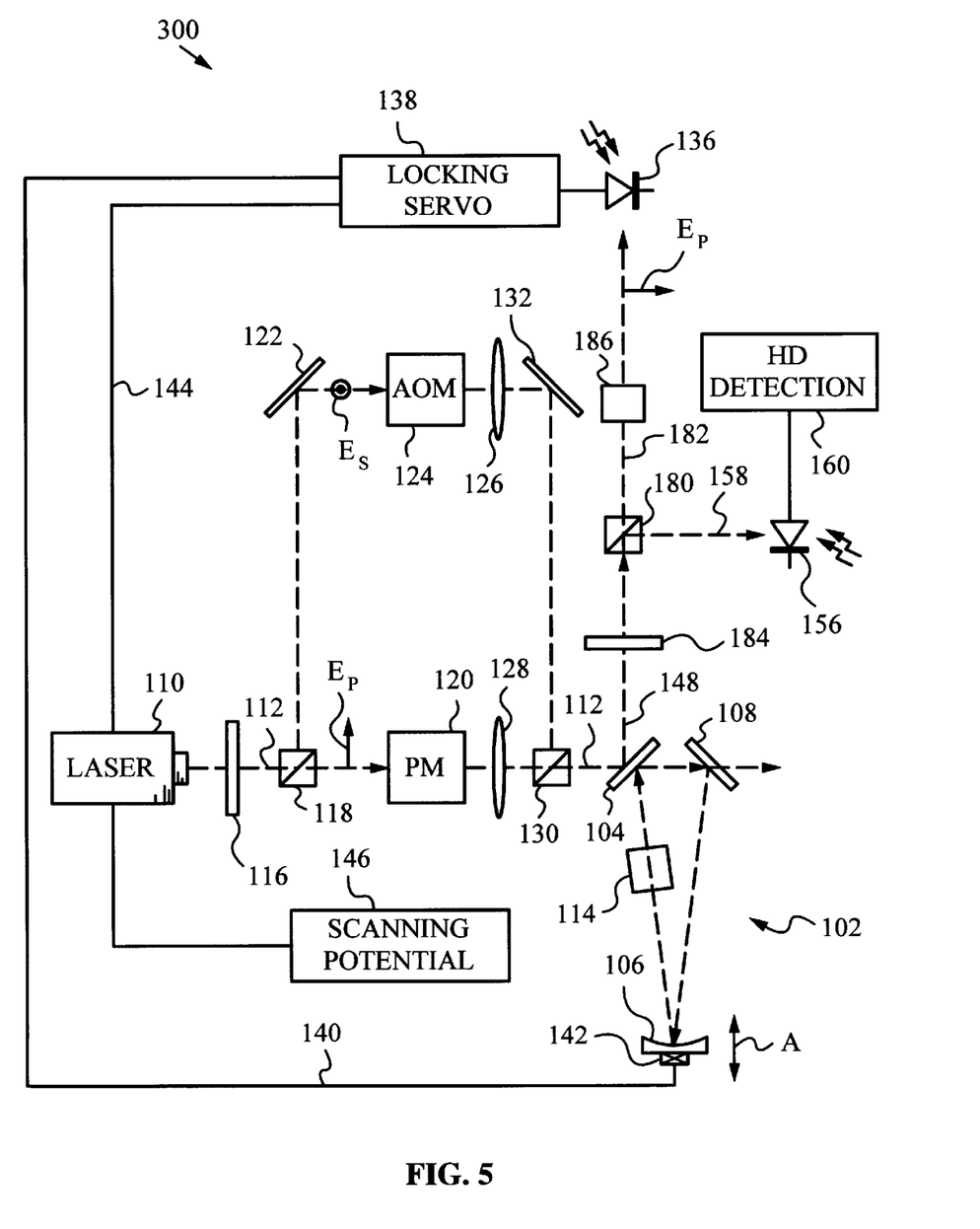
FIG. 5 is a schematic diagram of another alternative embodiment of a system according to the invention.

Another alternative cavity ring-down system 300 is illustrated in FIG. 5. System 300 is analogous to preferred system 100, with the exception that polarizations $E_P$ and $E_S$ reflected rather than transmitted by cavity 102 are used as ring-down beam 148. In this embodiment the ring-down phase is preferably initiated by AOM 124 through shifting signal frequency $\nu_{SIGNAL}$ of polarization $E_S$ acting as signal wave $E_{SIGNAL}$ to a value at which wave $E_S$ is no longer resonant in cavity 102.

A birefringent plate 184 and PBS 180 act as a combiner to overlap polarizations $E_S$ and $E_P$ of ring-down beam 148 in interference signal 158. A second interference signal 182 is transmitted by PBS 180. Since only polarization $E_P$ is used by locking servo 138, a filter 186 is placed in the path of interference signal 182 to filter out polarization $E_S$ based on its frequency. Thus, photodetector 136 receives polarization $E_P$ only and uses it for locking laser 110 to cavity 102 as in the previous embodiments.

Any of the frequency locked systems described above can be used for determination of the ring-up rate by the heterodyne technique. Because of intensity fluctuations during ring-up, laser to cavity locking or any other means of ensuring smooth light build-up in the ring-down cavity is required. The beginning of the measurement can coincide with the time when the AOM turns signal wave $E_{SIGNAL}$ on, e.g., after a ring-down has occurred.

In the ring-up embodiment, the waves generating the interference signal will be a ring-up wave $E_{RU}$ and the local oscillator wave $E_{LO}$. Of course, ring-up wave $E_{RU}$ will exhibit a growth rate $1/\tau$ rather than a decay rate. As before, the photodetector for receiving the interference signal is placed at a point of maximum overlap between the local oscillator wave $E_{LO}$ and the ring-up wave $E_{RU}$. The photodetector generates a heterodyne current $I_H$ corresponding to the heterodyne component of the interference signal. The heterodyne current $I_H$ has a second growth rate $1/2\tau$. Otherwise, the heterodyne detection technique is applied in the same manner as during ring-down.

It will be clear to one skilled in the art that the above embodiments may be altered in many ways without departing from the scope of the invention. For example, ring-down wave and local oscillator wave may have orthogonal but non-linear polarizations; e.g., they can have right-handed and left-handed circular polarizations. Also, the optics for overlapping ring-down wave with local oscillator wave can include other polarization rotating elements besides birefringent plates and polarizing beam splitters. For example, a person of average skill in the art will realize that Faraday rotators and half wave plates can be used for this purpose in alternative embodiments. Additional optics such as walk-off elements required for spatially separating the orthogonal polarizations before being rotated in, e.g. a Faraday rotator are well known in the art.

What is claimed is:

1. A cavity ring-down system for optical heterodyne detection of a ring-down wave $E_{RD}$ decaying at a first decay rate $1/\tau$, said system comprising:

a) a light source for providing a light beam;

b) a set of optics for generating from said light beam a local oscillator wave $E_{LO}$ at a local oscillator frequency $\nu_{LO}$ and a signal wave $E_{SIGNAL}$ at a signal frequency $\nu_{SIGNAL}$;

c) a ring-down cavity for receiving said local oscillator wave $E_{LO}$ and said signal wave $E_{SIGNAL}$;

d) a switching means for interrupting said signal wave $E_{SIGNAL}$ to initiate a ring-down phase during which said ring-down cavity issues said local oscillator wave $E_{LO}$ and said ring-down wave $E_{RD}$ at said signal frequency $\nu_{SIGNAL}$;

e) an optical combining means for overlapping said local oscillator wave $E_{LO}$ with said ring-down wave $E_{RD}$ to produce an interference signal having a heterodyne frequency related to a frequency difference $\delta\nu$ between said local oscillator frequency $\nu_{LO}$ and said signal frequency $\nu_{SIGNAL}$; and f) a photodetector for receiving said interference signal and generating a heterodyne current $I_H$ having a second decay rate $1/2\tau$.

2. The cavity ring-down system of claim 1, wherein said set of optics comprises a polarizing means for imparting said local oscillator wave $E_{LO}$ with a first polarization and imparting said ring-down wave $E_{RD}$ with a second polarization different from said first polarization.

3. The cavity ring-down system of claim 2, wherein said optical combining means comprises one or more elements selected from the group consisting of polarization rotators, linear birefringent elements, circular birefringent elements, beam splitters and waveplates.

4. The cavity ring-down system of claim 2, wherein said light source is a continuous wave laser.

5. The cavity ring-down system of claim 4 further comprising a locking means for locking said ring-down cavity to said continuous wave laser using said local oscillator wave $E_{LO}$.

6. The cavity ring-down system of claim 1 wherein said photodetector is selected from the group consisting of photodiodes and phototransistors.

7. The cavity ring-down system of claim 1, wherein the intensity of said local oscillator wave $E_{LO}$ is larger than an initial intensity of said ring-down wave $E_{RD}$.

8. The cavity ring-down system of claim 1, wherein said frequency difference $\delta\nu$ is equal to the frequency difference between different modes of said ring-down cavity.

9. The cavity ring-down system of claim 1, wherein said frequency difference $\delta\nu$ is equal to the frequency difference between two polarizations of the same mode of said ring-down cavity.

10. The cavity ring-down system of claim 1, wherein said frequency difference $\delta\nu$ is equal to an integral multiple of the free spectral range of said ring-down cavity.

11. The cavity ring-down system of claim 1, further comprising a phase adjustment means for adjusting the phase between said local oscillator wave $E_{LO}$ and said ring-down wave $E_{RD}$.

12. The cavity ring-down system of claim 11, wherein said frequency difference $\delta\nu$ is approximately zero.

13. The cavity ring-down system of claim 1, further comprising a frequency adjustment means for adjusting said frequency difference $\delta\nu$.

14. The cavity ring-down system of claim 13, wherein said frequency adjustment means is an acousto-optic modulator.

15. The cavity ring-down system of claim 1, wherein said ring-down cavity is a ring resonator.

16. The cavity ring-down system of claim 1, wherein said switching means is an acousto-optic modulator.

17. A cavity ring-down system for optical heterodyne detection of a ring-down wave $E_{RD}$ decaying at a first decay rate $1/\tau$, said system comprising:

a) a light source for providing a light beam;

b) a set of optics for generating from said light beam a local oscillator wave $E_{LO}$ at a local oscillator frequency $\nu_{LO}$ and a signal wave $E_{SIGNAL}$ at a signal frequency $\nu_{SIGNAL}$;

c) a ring-down cavity for receiving said local oscillator wave $E_{LO}$ and said signal wave $E_{SIGNAL}$;

d) a switching means for altering said signal frequency $\nu_{SIGNAL}$ of said signal wave $E_{SIGNAL}$ to initiate a ring-down phase during which said ring-down cavity issues said local oscillator wave $E_{LO}$ and said ring-down wave $E_{RD}$ at said signal frequency $\nu_{SIGNAL}$;

e) an optical combining means for overlapping said local oscillator wave $E_{LO}$ with said ring-down wave $E_{RD}$ to produce an interference signal having a heterodyne frequency related to a frequency difference $\delta\nu$ between said local oscillator frequency $\nu_{LO}$ and said signal frequency $\nu_{SIGNAL}$; and f) a photodetector for receiving said interference signal and generating a heterodyne current $I_H$ having a second decay rate $1/2\tau$.

18. The cavity ring-down system of claim 17, wherein said set of optics comprises a polarizing means for imparting said local oscillator wave $E_{LO}$ with a first polarization and imparting said ring-down wave $E_{RD}$ with a second polarization different from said first polarization.

19. The cavity ring-down system of claim 18, wherein said optical combining means comprises one or more elements selected from the group consisting of polarization rotators, linear birefringent elements, circular birefringent elements, beam splitters and waveplates.

20. The cavity ring-down system of claim 18, wherein said light source is a continuous wave laser.

21. The cavity ring-down system of claim 20 further comprising a locking means for locking said ring-down cavity to said continuous wave laser using said local oscillator wave $E_{LO}$.

22. The cavity ring-down system of claim 17, wherein said photodetector is selected from the group consisting of photodiodes and phototransistors.

23. The cavity ring-down system of claim 17, wherein the intensity of said local oscillator wave $E_{LO}$ is larger than an initial intensity of said ring-down wave $E_{RD}$.

24. The cavity ring-down system of claim 17, wherein said frequency difference $\delta\nu$ is equal to the frequency difference between different modes of said ring-down cavity.

25. The cavity ring-down system of claim 17, wherein said frequency difference $\delta\nu$ is equal to the frequency difference between two polarizations of the same mode of said ring-down cavity.

26. The cavity ring-down system of claim 17, wherein said frequency difference $\delta\nu$ is equal to an integral multiple of the free spectral range of said ring-down cavity.

27. The cavity ring-down system of claim 17, further comprising a phase adjustment means for adjusting the phase between said local oscillator wave $E_{LO}$ and said ring-down wave $E_{RD}$.

28. The cavity ring-down system of claim 27, wherein said frequency difference $\delta\nu$ is approximately zero.

29. The cavity ring-down system of claim 17, further comprising a frequency adjustment means for adjusting said frequency difference $\delta\nu$.

30. The cavity ring-down system of claim 29, wherein said frequency adjustment means is an acousto-optic modulator.

31. The cavity ring-down system of claim 17, wherein said ring-down cavity is a ring resonator.

32. The cavity ring-down system of claim 17, wherein said switching means is an acousto-optic modulator.

33. A cavity ring-down system for optical heterodyne detection of a ring-up wave $E_{RU}$ growing at a first growth rate $1/\tau$, said system comprising:

a) a light source for providing a light beam;

b) a set of optics for generating from said light beam a local oscillator wave $E_{LO}$ at a local oscillator frequency $\nu_{LO}$ and a signal wave $E_{SIGNAL}$ at a signal frequency $\nu_{SIGNAL}$;

c) a ring-down cavity for receiving said local oscillator wave $E_{LO}$ and said signal wave $E_{SIGNAL}$;

d) a switching means for turning on said signal wave $E_{SIGNAL}$ to initiate a ring-up phase during which said ring-down cavity issues said local oscillator wave $E_{LO}$ and said ring-up wave $E_{RU}$ at said signal frequency $\nu_{SIGNAL}$;

e) an optical combining means for overlapping said local oscillator wave $E_{LO}$ with said ring-up wave $E_{RU}$ to produce an interference signal having a heterodyne frequency related to a frequency difference $\delta\nu$ between said local oscillator frequency $\nu_{LO}$ and said signal frequency $\nu_{SIGNAL}$; and f) a photodetector for receiving said interference signal and generating a heterodyne current $I_H$ having a second growth rate $1/2\tau$.

34. The cavity ring-down system of claim 33, wherein said set of optics comprises a polarizing means for imparting said local oscillator wave $E_{LO}$ with a first polarization and imparting said ring-up wave $E_{RU}$ with a second polarization different from said first polarization.

35. A cavity ring-down system for optical heterodyne detection of a ring-up wave $E_{RU}$ growing at a first growth rate $1/\tau$, said system comprising:

a) a light source for providing a light beam;

b) a set of optics for generating from said light beam a local oscillator wave $E_{LO}$ at a local oscillator frequency $\nu_{LO}$ and a signal wave $E_{SIGNAL}$ at a signal frequency $\nu_{SIGNAL}$;

c) a ring-down cavity for receiving said local oscillator wave $E_{LO}$ and said signal wave $E_{SIGNAL}$;

d) a switching means for altering said signal frequency $\nu_{SIGNAL}$ of said signal wave $E_{SIGNAL}$ to initiate a ring-up phase during which said ring-down cavity issues said local oscillator wave $E_{LO}$ and said ring-up wave $E_{RU}$ at said signal frequency $\nu_{SIGNAL}$;

e) an optical combining means for overlapping said local oscillator wave $E_{LO}$ with said ring-up wave $E_{RU}$ to produce an interference signal having a heterodyne frequency related to a frequency difference $\delta\nu$ between said local oscillator frequency $\nu_{LO}$ and said signal frequency $\nu_{SIGNAL}$; and f) a photodetector for receiving said interference signal and generating a heterodyne current $I_H$ having a second growth rate $1/2\tau$.

36. The cavity ring-down system of claim 35, wherein said set of optics comprises a polarizing means for imparting said local oscillator wave $E_{LO}$ with a first polarization and imparting said ring-up wave $E_{RU}$ with a second polarization different from said first polarization.

* * * * *